US00PP16773P2

(12) United States Plant Patent
Yates

(10) Patent No.: US PP16,773 P2
(45) Date of Patent: Jul. 4, 2006

(54) ***PENSTEMON* PLANT NAMED 'YAPUT'**

(50) Latin Name: *Penstemon kunthii*
Varietal Denomination: YAPUT

(76) Inventor: Frederic Charles Yates, A.T. Yates & Son The Poplars Nursery, Congleton, Cheshire (GB), CW124SP ( * ) Notice: Subject to any disclaimer, the term of this patent is extended or adjusted under 35 U.S.C. 154(b) by 90 days.

(21) Appl. No.: 11/053,535

(22) Filed: Feb. 7, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new and distinct cultivar of *Penstemon* plant named 'Yaput' that is characterized by compact upright habit, dark green glossy leaves, and fragrant flowers that are dark pink in color with white throats that exhibit dark pink stripes. In combination these characteristics set 'Yaput' apart from all other existing varieties of *Penstemon* known to the inventor.

3 Drawing Sheets

Genus: *Penstemon.*
Species: *kunthii.*
Denomination: Yaput.

BACKGROUND OF THE INVENTION

The present invention relates to a new and distinct cultivar of *Penstemon* plant that is grown for use as an ornamental perennial for bedding or containers. The new cultivar is known botanically as *Penstemon kunthii* and that will be referred to hereinafter by the cultivar name 'Yaput'.

'Yaput' resulted from a long term breeding program that was conducted by the inventor at the inventor's nursery in Congleton, Cheshire, United Kingdom and begun in 1993. The purpose of the breeding program was to produce varieties of *Penstemon* that exhibit new and unique habit and flower color. In 1993, the inventor acquired seed of the species *Penstemon kunthii*, sowed that seed and selected a single plant for its promising branching habit as a subject for further cross-pollination and back-crossing which took place over three generations during the three year period, 1994 to 1996. In 1996, the inventor discarded all but a few plants from the accumulated population and in spring 1997 asexually reproduced the remainder in order to evaluate the characteristics of each when grown from a cutting as would be typical in commercial production. In the summer of 1997, the inventor selected a single plant from the cutting-raised population, which plant is the subject of the present invention 'Yaput'. Selection of 'Yaput' was based on new and unique habit and flower color. No other plants were selected from the breeding program.

Both the female and the male parents are unnamed and unreleased plants raised by the inventor from seed harvested by the inventor as a result of deliberate cross-pollinations of plants whose origin was seed collected from an unnamed plant of *Penstemon kunthii*. 'Yaput' was selected, and is distinguishable from the parent plants, by habit and flower color. The distinguishing characteristics of 'Yaput' are compact upright habit, dark green glossy leaves, and fragrant flowers that are dark pink in color with white throats that exhibit red-purple stripes. The closest comparison plant is

*Penstemon kunthii*. 'Yaput' differs from the comparison plant in habit and flower color.

'Yaput' was first asexually propagated by the inventor in 1997 at the inventor's nursery in Congleton, Cheshire, England using tip cuttings. 'Yaput' has been found stable and true to type after many cycles of vegetative cuttings.

SUMMARY OF THE INVENTION

The following traits have been repeatedly observed and represent the distinguishing characteristics of 'Yaput'. In combination these traits set the new cultivar apart from all other existing varieties of *Penstemon* known to the inventor. 'Yaput' has not been tested under all possible conditions and phenotypic differences may be observed with variations in environmental, climatic, and cultural conditions, however, without any variance in genotype.

1. *Penstemon* 'Yaput' exhibits a compact upright habit.
2. *Penstemon* 'Yaput' exhibits flowers that are dark pink in color with white throats that exhibit dark pink stripes.
2. The flowers of *Penstemon* 'Yaput' are fragrant.
3. The flowers of *Penstemon* 'Yaput' exhibit short corolla tubes.
4. *Penstemon* 'Yaput' is free flowering.
5. *Penstemon* 'Yaput' exhibits dark green glossy leaves.
6. *Penstemon* 'Yaput' is hardy to USDA Zone 4.
7. *Penstemon* 'Yaput' is vigorous.
8. *Penstemon* 'Yaput' is 50 cm. in height and 30 cm. in width at maturity.

BRIEF DESCRIPTION OF THE DRAWINGS

The accompanying color drawings illustrate the overall appearance of the new *Penstemon* cultivar 'Yaput' showing the colors as true as it is reasonably possible to obtain in colored reproductions of this type. Colors in the drawings may differ from the color values cited in the detailed botanical description, which accurately describe the actual colors of the new variety of *Penstemon* named 'Yaput'.

The drawing labeled as FIG. 1 depicts a five month old single plant of 'Yaput' that had been started as a tip cutting in early spring, transplanted to a 1 liter (5 inch diameter) container and pinched once at approximately the third node to encourage basal and lateral branching. close-up view of the flowers.

The drawing labeled as FIG. 2 depicts a close-up view of the flowers of 'Yaput' and showing their outer dark pink coloration, and inner throats of white with occasional red-purple fine lining at the base of the lobe.

The drawing labeled as FIG. 3 depicts a whole plant of 'YAPUT' in full bloom in mid summer, and showing the dense floriferous habit which is typical of 'Yaput' and atypical of the genus *Penstemon* whose species and cultivars are generally taller, have a more open habit and are more sparsely flowering.

BOTANICAL DESCRIPTION OF THE PLANT

Figure 1:
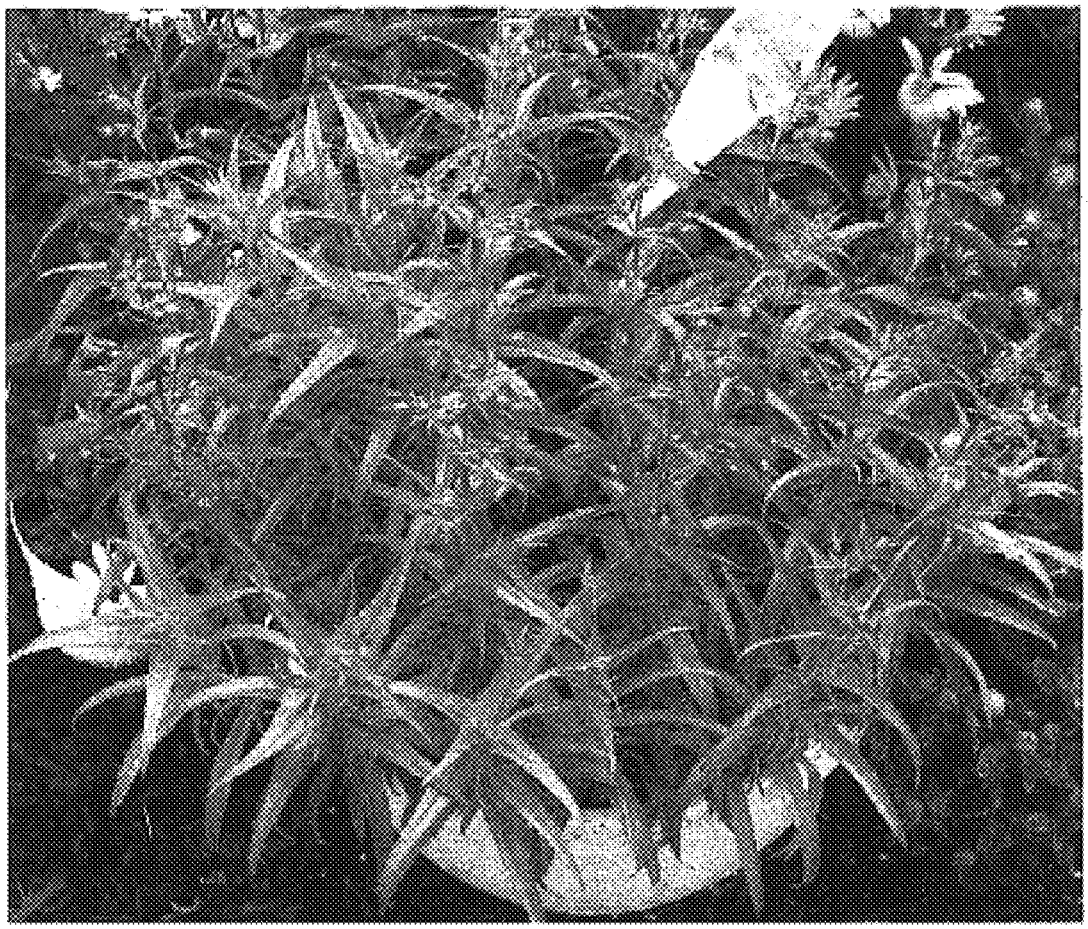
FIG. 1 was made from a digital photographic image of a plant of 'Yaput' grown in the spring and summer out of doors in Bonsall, southern California.
Figure 2:
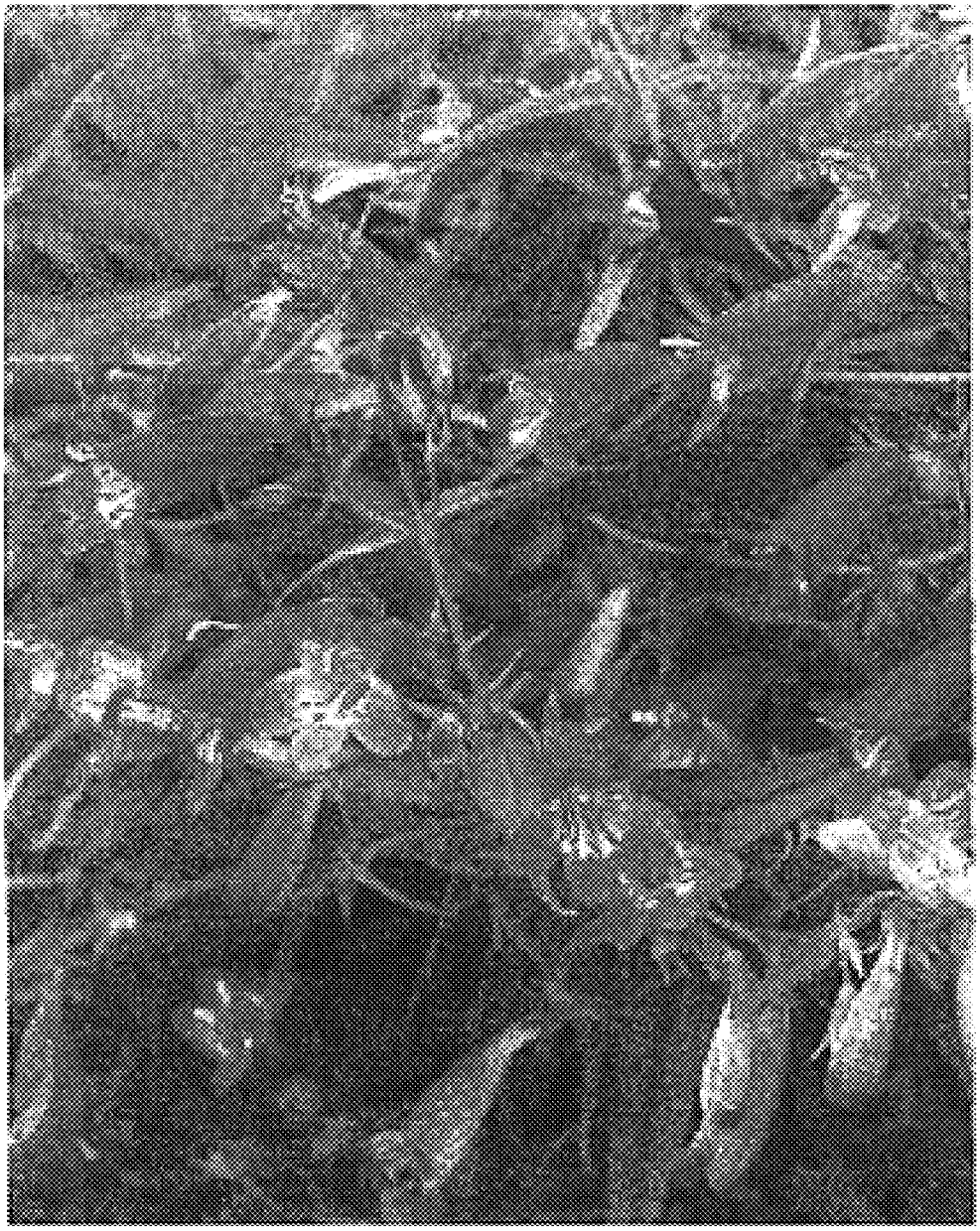
FIG. 2 was made from a digital photographic image of the flowers on a six month old plant of 'Yaput' grown in the spring and summer out of doors in Bonsall, southern California.
Figure 3:
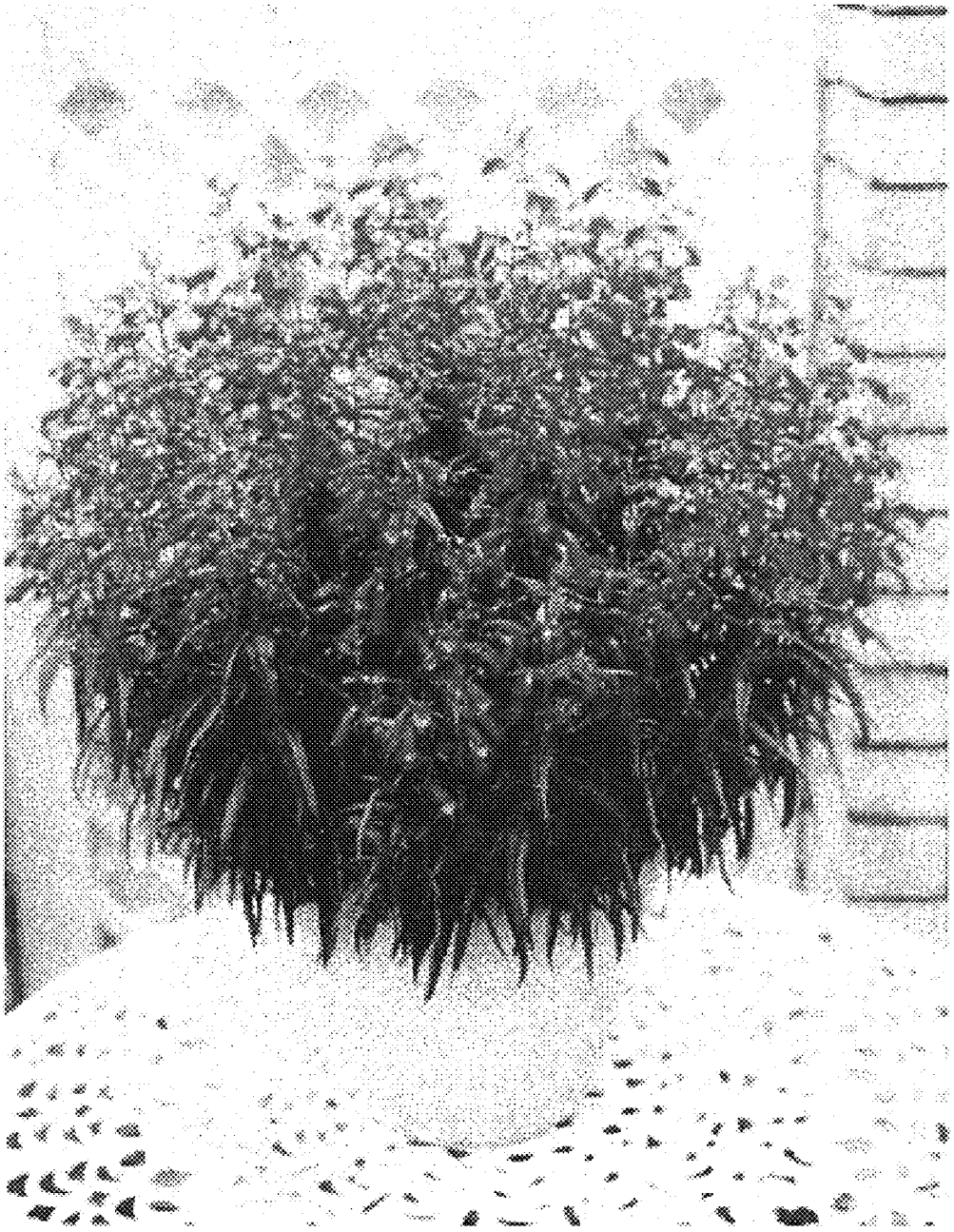
FIG. 3 was made from a traditional 25 mm color transparency taken by the inventor in the inventor's greenhouse in Congleton, Cheshire, England.

The following is a detailed description of the new *Penstemon* plant named 'Yaput'. Data was collected in Arroyo Grande, Calif. from plants approximately three to five months old from a cutting. The plants were grown in an unheated greenhouse in 10 cm diameter containers. Phenotypic differences may be observed with variations in environmental, climatic, and cultural conditions, however without any difference in genotype. The color determinations are in accordance with the 2001 Edition of the Colour Chart of The Royal Horticultural Society, London, England, except where general color terms of ordinary dictionary significance are used. The growing requirements are similar to other *Penstemon* plants.

Botanical classification: *Penstemon* 'Yaput'.
Genus: *Penstemon.*
Species: *kunthii.*
Denomination: 'Yaput'.
Commercial classification: Ornamental perennial.
Common name: *Penstemon.*
Use: Bedding and container plant.
Commercial container size: Suggested size for a same-season finished plant is a 1 liter to 1.5 liter container, with a diameter of 10 cm to 15 cm. Pinching will be required to maintain a mounding habit in a full season plant.
Cultural requirements: Plant in full sun, freely draining soil and provide moderate water.
Parentage: 'Yaput' is a seedling selection that resulted from the deliberate cross-pollination of the following parent plants:
- *Female parent.*—One unnamed plant of *Penstemon kunthii.*
- *Male parent.*—One unnamed plant of *Penstemon kunthii.*

Plant description:
Blooming seasons: Summer and early fall.
Plant habit: Compact upright habit.
Plant type: Evergreen perennial.
Vigor: Moderate.
Plant height (at maturity): 50 cm. in height at maturity.
Plant width (at maturity): 30 cm. in width at maturity.
Hardiness: USDA Zone 4.
Root system: Fine roots.
Propagation: Tip cuttings.
Time to initiate roots: Approximately 10 days is needed to develop roots on an initial cutting.
Temperature to initiate roots: Recommended air temperatures to develop roots on initial cutting is from 20° to 22° Centigrade.
Crop time: From 14–16 weeks are needed to produce a commercial size container with plants in first bud and bloom.
Light requirements: Natural daylight.
Disease and pest susceptibility and resistance: No particular susceptibility or resistance to any disease or pest has been noted on 'Yaput'. *Penstemons* generally are considered relatively trouble-free as garden plants.
Stem:
- *Stem shape.*—Cylindrical.
- *Stem length.*—25 cm.
- *Stem diameter.*—2 mm.
- *Stem surface.*—Puberulent.
- *Stem surface appearance.*—Glossy.
- *Stem color.*—143A.
- *Internode length.*—4 cm. between nodes.

Foliage:
- *Leaf arrangement.*—A combination of opposite and whorled leaf arrangement on an individual whole plant.
- *Leaf shape.*—Lanceolate.
- *Leaf division.*—Simple.
- *Leaf apex.*—Acute.
- *Leaf base.*—Truncate.
- *Leaf margins.*—Closest to crenate.
- *Leaf surfaces* (*adaxial and abaxial*).—Glabrous.
- *Leaf appearance* (*abaxial surface*).—Abaxial surfaces have a matte appearance.
- *Leaf appearance* (*adaxial surface*).—Adaxial surfaces have a glossy appearance.
- *Leaf arrangement.*—A combination of opposite and whorled.
- *Leaf length.*—Leaves on an individual whole plant range from 3.50 cm. to 6 cm. in length.
- *Leaf width.*—Leaves on an individual whole plant range from 0.50 cm. to 1.25 cm. in width.
- *Leaf color* (*adaxial surface*).—139A.
- *Leaf color* (*abaxial surface*).—139B.
- *Leaf attachment.*—Sessile.
- *Vein color* (*adaxial surface*).—139C.
- *Vein color* (*abaxial surface*).—139C.
- *Vein pattern.*—Pinnate.

Flowers:
- *Type of inflorescence.*—Panicle.
- *Quantity of flowers per inflorescence.*—An average of 15 per inflorescence.
- *Flowering season.*—Summer and early fall.
- *Fragrance.*—Sweet fragrance observed.
- *Self-cleaning or persistent.*—Self-cleaning.
- *Inflorescence dimensions.*—Average dimensions of an individual inflorescence on an individual whole plant are 9 cm. in height, and 7 cm. in width.
- *Number of flowers per container plant.*—An average of 35 flowers per 10-centimeter container plant.
- *Number of buds per container plant.*—An average of 20 buds per 10-centimeter container plant.

*Peduncle dimensions.*—7 cm. in length and 1.50 mm. in diameter.
*Peduncle color.*—143A.
*Peduncle surface.*—Stipitate glandular.
*Peduncle shape.*—Cylindrical.
*Pedicels.*—Present.
*Pedicel dimensions.*—9 mm. in length and 0.50 mm. in diameter.
*Pedicel surface.*—Puberulent.
*Pedicel color.*—Individual colors 187A and 143A are present on an individual pedicel.
*Bud shape.*—Obelliptic.
*Bud apex.*—Closest to obtuse.
*Bud surface.*—Pubescent.
*Bud color.*—71C.
*Bud dimensions.*—1 cm. in length and 0.50 cm. in width.
*Flower shape.*—Tubular.
*Flower color.*—Colors 71A and 155A are individually present.
*Flower depth.*—3 cm. in depth.
*Flower diameter.*—1.50 cm. in diameter.
*Corolla tube depth.*—1.50 cm. in depth.
*Corolla tube diameter.*—0.75 cm. in diameter.
*Petals fused or unfused.*—Petals are basally fused.
*Number of petals.*—Five.
*Petal color* (*abaxial and adaxial surfaces*).—71A.
*Corolla tube color* (*inside surface*).—White 155A with occasional red-purple 58B fine lines (less than 0.25 mm in width and approximately 3 mm–5 mm in length) running from base of abaxial surface of lobe into the tube.
*Corolla tube color* (*outside surface*).—58B.
*Petal surfaces* (*adaxial and abaxial surfaces*).—Glabrous.
*Petal apex.*—Petal apex is mostly rounded, but can range to retuse on an individual plant.
*Petal margins.*—Entire.
*Calyx shape.*—Stellate.
*Number of sepals.*—Five.
*Sepal dimensions.*—6 mm. in length and 2 mm. in width.
*Sepals fused or unfused.*—Unfused.
*Sepal surface* (*adaxial surface*).—Puberulent.
*Sepal surface* (*abaxial surface*).—Puberulent.
*Sepal apex.*—Acute.
*Sepal base.*—Truncate.
*Sepal margins.*—Entire.
*Sepal color* (*adaxial surface*).—Individual colors 187A and 143A are present on an individual sepal.
*Sepal color* (*abaxial surface*).—Individual colors 187A and 143A are present on an individual sepal.
*Lastingness of individual flower.*—An individual flower will last 5–10 days.

Reproductive organs:
*Stamens.*—Four stamens present.
*Color of stamens.*—155A.
*Stamen dimensions.*—2 cm. in length and 0.5 mm. in diameter.
*Anther color.*—70A.
*Anther dimensions.*—2.50 mm. in length and 2.75 mm. in diameter.
*Amount of pollen.*—Low.
*Color of pollen.*—70A.
*Anther shape.*—Heart shaped.
*Pistil.*—Present.
*Pistil number.*—One pistil present per individual flower.
*Pistil color.*—155A.
*Pistil dimensions.*—2.25 cm. in length and 0.5 mm. in width.
*Pistil shape.*—Filament.
*Pistil surface.*—Glabrous.
*Stigma color.*—155A.
*Stigma surface.*—Glabrous.
*Stigma dimensions.*—0.5 cm. in length and 0.5 cm. in width.
*Nectary.*—Adnate to inside of corolla tube.
*Nectary shape.*—Filament.
*Nectary dimensions.*—2 cm. in length and 0.5 mm. in width.
*Nectary color.*—155A.
*Nectary surface.*—Glabrous except for tip, which has yellow hairs the color of 14A. Ovary dimensions 4 mm. in length and 3 mm. in width.
*Ovary shape.*—Oval.
*Ovary position.*—Superior.
*Ovary color.*—144B.

Seed production: None observed to date.

What is claimed is:

1. A new and distinct cultivar of *Penstemon* plant named 'Yaput' as described and illustrated herein.

* * * * *